US010234395B2

United States Patent
Gargas et al.

(10) Patent No.: US 10,234,395 B2
(45) Date of Patent: Mar. 19, 2019

(54) RAMAN APPARATUS AND METHODS

(71) Applicant: Seagate Technology LLC, Cupertino, CA (US)

(72) Inventors: Daniel J. Gargas, San Francisco, CA (US); David M. Tung, Livermore, CA (US); Travis W. Grodt, Fremont, CA (US); Joachim W. Ahner, Livermore, CA (US)

(73) Assignee: Seagate Technology LLC, Cupertino, CA (US)

( * ) Notice: Subject to any disclaimer, the term of this patent is extended or adjusted under 35 U.S.C. 154(b) by 206 days.

(21) Appl. No.: 14/834,418

(22) Filed: Aug. 24, 2015

(65) Prior Publication Data

US 2016/0077009 A1 Mar. 17, 2016

Related U.S. Application Data

(60) Provisional application No. 62/050,020, filed on Sep. 12, 2014.

(51) Int. Cl.
| | |
|---|---|
| G01N 21/65 | (2006.01) |
| G01N 21/84 | (2006.01) |
| G01N 21/95 | (2006.01) |

(52) U.S. Cl.
CPC ......... G01N 21/65 (2013.01); G01N 21/8422 (2013.01); *G01N 21/95* (2013.01); *G01N 2201/0833* (2013.01)

(58) Field of Classification Search
CPC .................................................... G01N 21/65
USPC ....................................................... 356/301
See application file for complete search history.

(56) References Cited

U.S. PATENT DOCUMENTS

| | | | |
|---|---|---|---|
| 4,030,827 A | 6/1977 | Delhaye et al. | |
| 4,195,930 A | 4/1980 | Delhaye et al. | |
| 6,097,741 A * | 8/2000 | Lin | H01S 3/067 372/6 |
| 7,403,273 B2 | 7/2008 | Treado et al. | |
| 7,408,636 B2 | 8/2008 | Tuschel et al. | |
| 7,433,031 B2 | 10/2008 | Xu et al. | |
| 7,433,056 B1 * | 10/2008 | Janik | G01B 11/0616 356/301 |
| 7,777,876 B2 | 8/2010 | Horai et al. | |
| 7,945,077 B2 | 5/2011 | Demos | |
| 8,467,048 B2 | 6/2013 | Nishiyama et al. | |
| 2002/0109110 A1 | 8/2002 | Some et al. | |
| 2005/0094864 A1 | 5/2005 | Xu et al. | |
| 2005/0105791 A1 | 5/2005 | Lee et al. | |
| 2006/0001869 A1 | 1/2006 | Tuschel et al. | |

(Continued)

OTHER PUBLICATIONS

"Measuring the tensor nature of stress in silicon using polarized off-axis Raman spectroscopy" Appl. Phys. Lett. 66 (26), Jun. 26, 1995.

*Primary Examiner* — Tarifur Chowdhury
*Assistant Examiner* — Omar Nixon

(57) ABSTRACT

Provided herein is an apparatus, including an excitation arm including excitation optics; a collection arm including collection optics, wherein the excitation arm and the collection arm are geometrically off-axis from one another for independent control of the excitation optics or the collection optics; and a full-surface spectroscopic analyzer to analyze a thin-film over an article from Raman-scattered light collected by the collection optics.

16 Claims, 12 Drawing Sheets

(56) References Cited

U.S. PATENT DOCUMENTS

| | | | |
|---|---|---|---|
| 2009/0246904 A1* | 10/2009 | Psyk | B23K 26/36 |
| | | | 438/57 |
| 2009/0306521 A1* | 12/2009 | Ermakov | A61B 5/0075 |
| | | | 600/477 |
| 2011/0292157 A1* | 12/2011 | Ghauri | B23K 26/0066 |
| | | | 347/255 |
| 2014/0098364 A1* | 4/2014 | Ahner | G01N 21/63 |
| | | | 356/237.2 |

* cited by examiner

EXCITATION ARM 120

RAMAN APPARATUS AND METHODS

CROSS-REFERENCE TO RELATED APPLICATIONS

This application claims the benefit of U.S. Provisional Patent Application No. 62/050,020, filed Sep. 12, 2014, which is incorporated herein by reference in its entirety.

BACKGROUND

An article may be inspected for features, including defects that might degrade the performance of the article or a system including the article. For example, a hard disk for a hard disk drive may be fabricated on a production line and inspected for defects that might degrade the performance of the disk or the hard disk drive. Accordingly, apparatuses and methods may be used to inspect articles for features.

SUMMARY

Provided herein is an apparatus, including an excitation arm including excitation optics; a collection arm including collection optics, wherein the excitation arm and the collection arm are geometrically off-axis from one another for independent control of the excitation optics or the collection optics; and a processing means for processing Raman-scattered light collected by the collection optics and providing a full-surface spectroscopic analysis of a thin-film over an article.

These and other features and aspects of the concepts provided herein may be better understood with reference to the following drawings, description, appendices, and appended claims.

DRAWINGS

Figure 1:
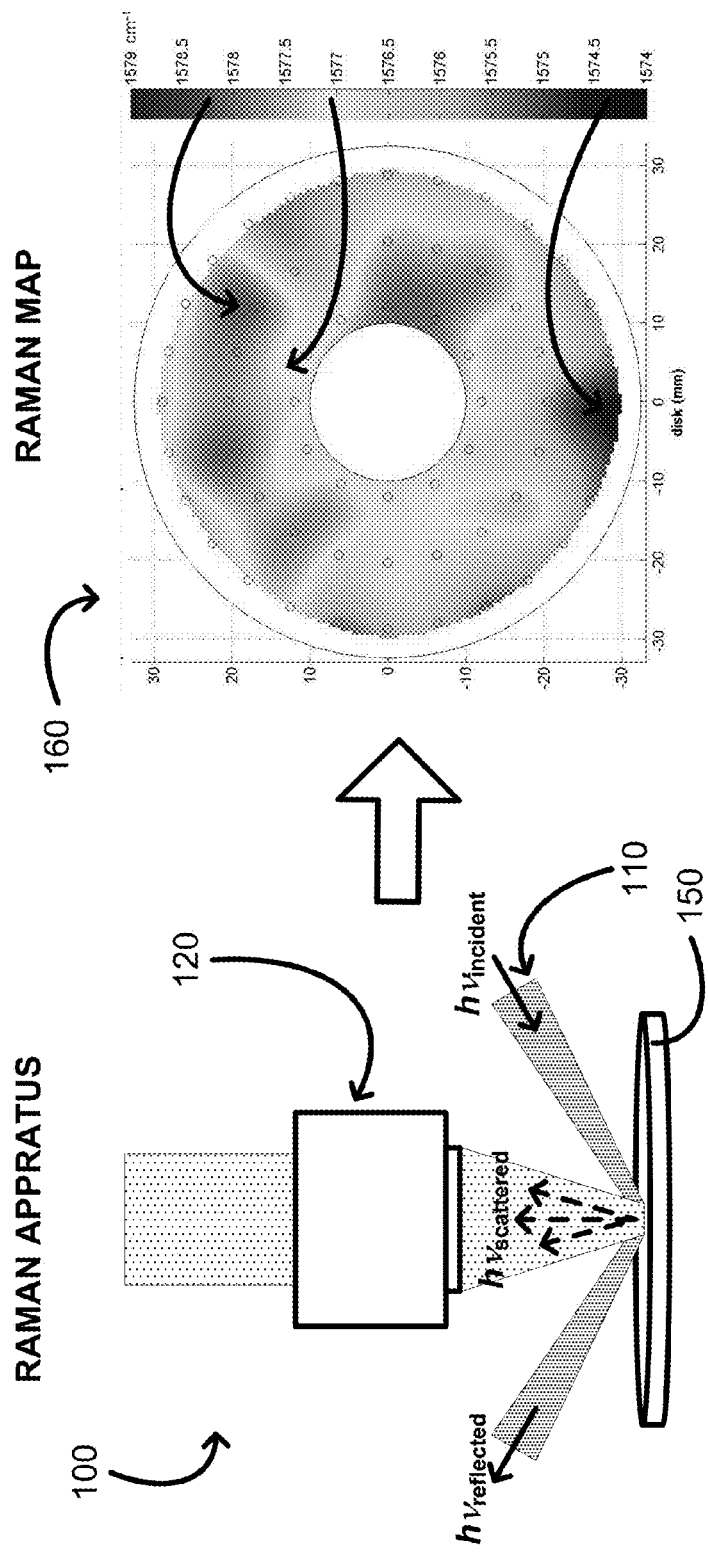

FIG. 1 provides a schematic illustrating a Raman apparatus and a Raman map according to one or more embodiments.

Figure 2A:
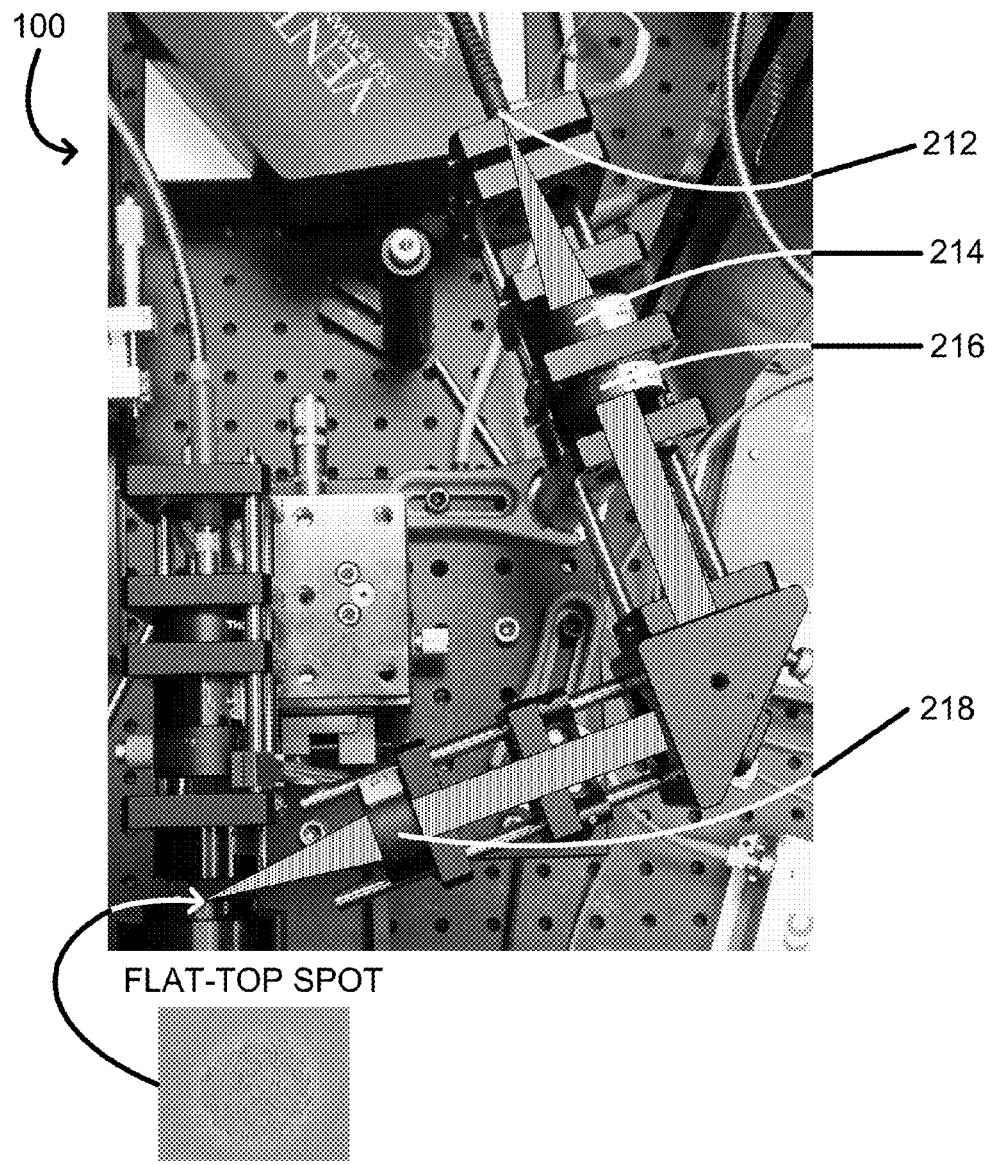

FIG. 2A provides an annotated image of an excitation arm of a Raman apparatus according to one or more embodiments.

Figure 2B:
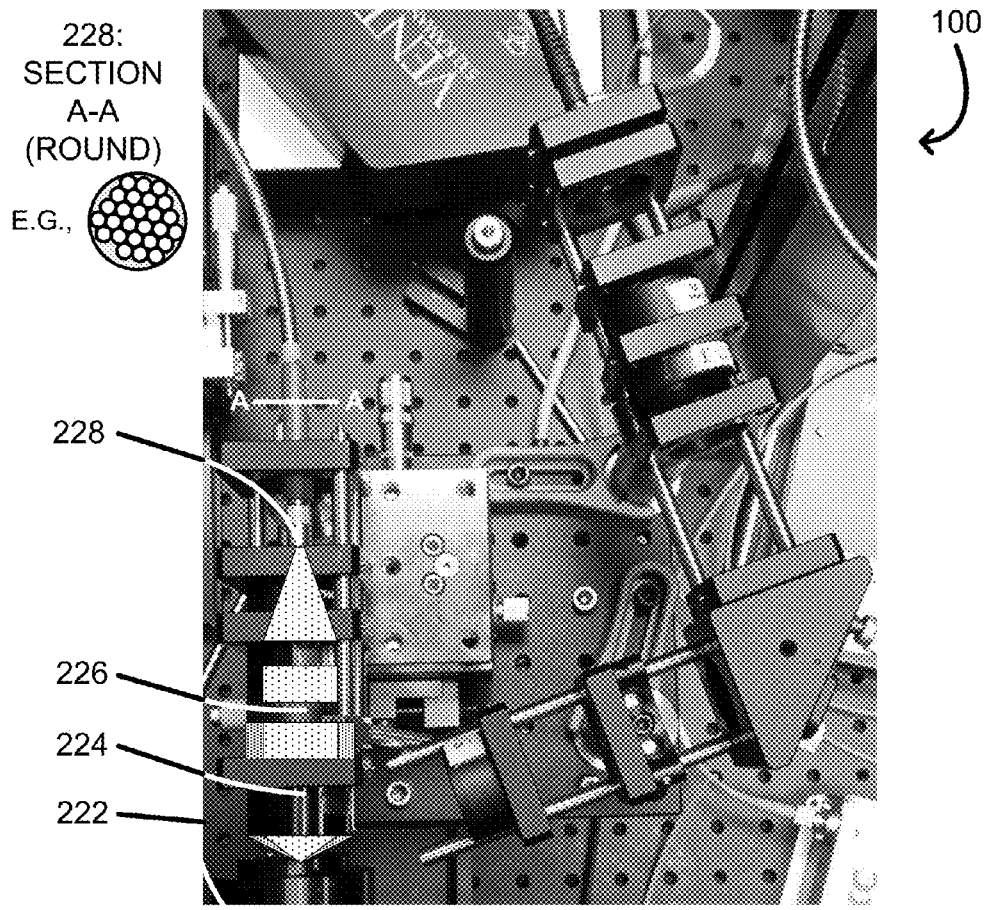

FIG. 2B provides an annotated image of a collection arm of a Raman apparatus according to one or more embodiments.

Figure 2C:
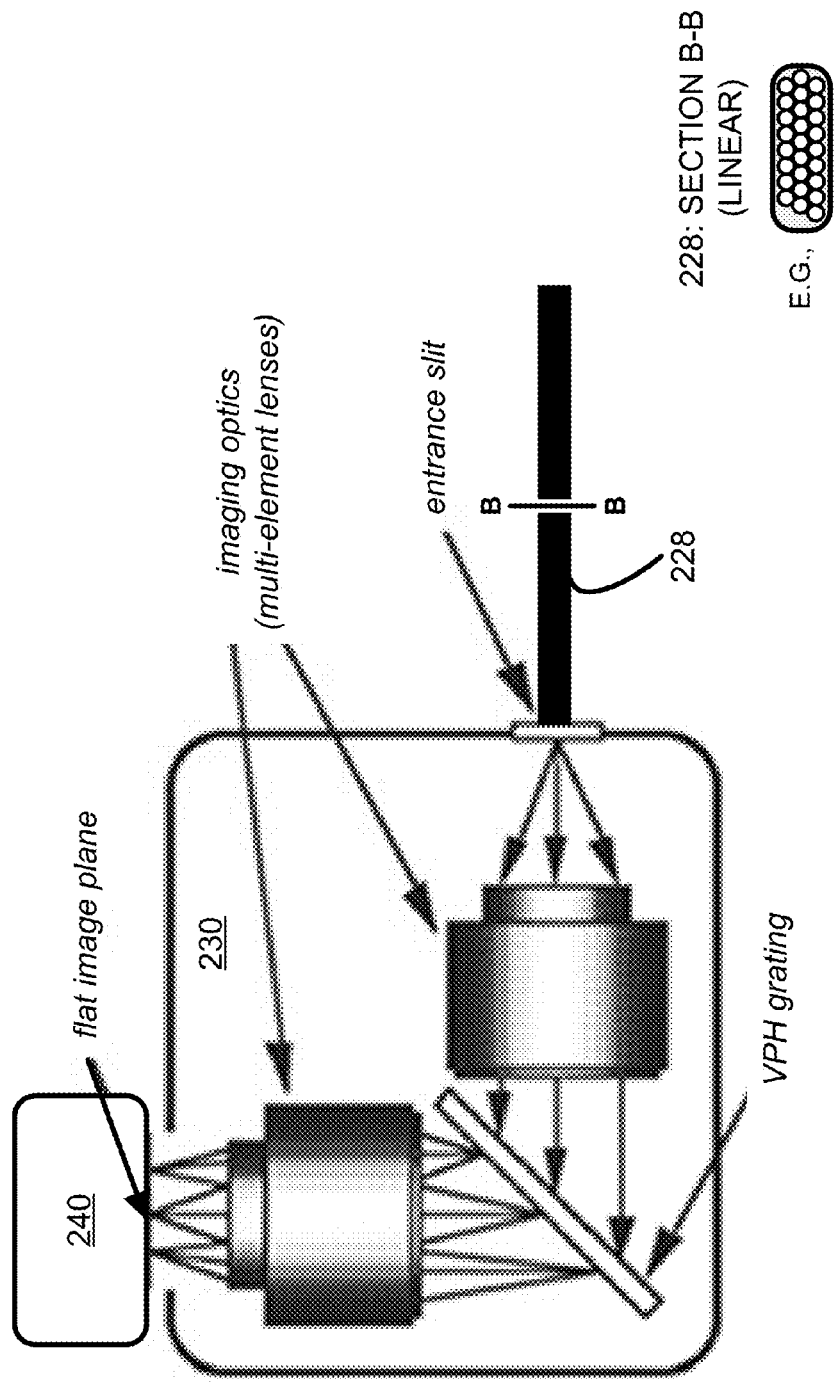

FIG. 2C provides a schematic illustrating a spectrometer for a Raman apparatus according to one or more embodiments.

Figure 2D:
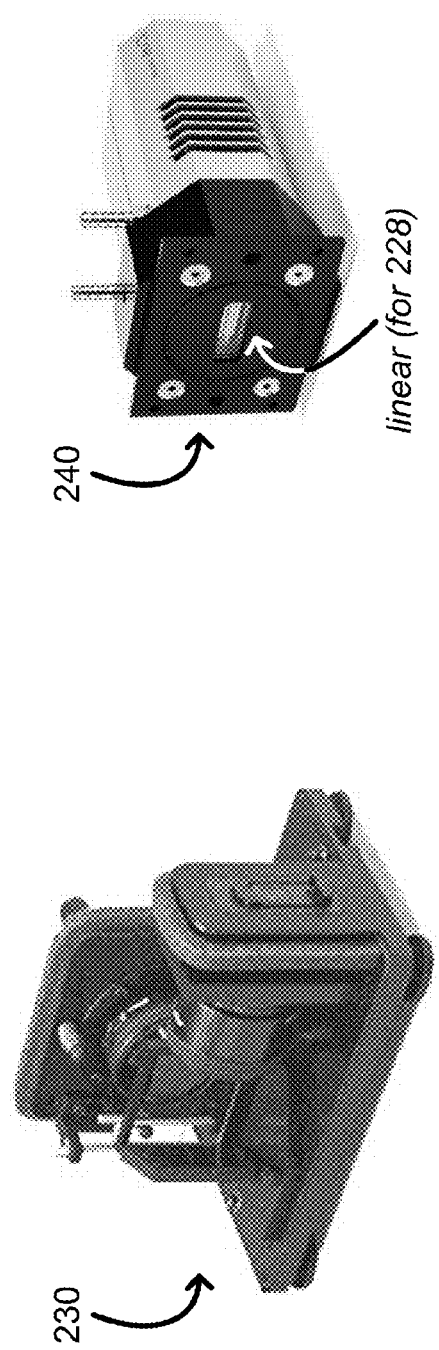

FIG. 2D provides a schematic illustrating a Raman spectroscopy system for a Raman apparatus according to one or more embodiments.

Figure 3A:
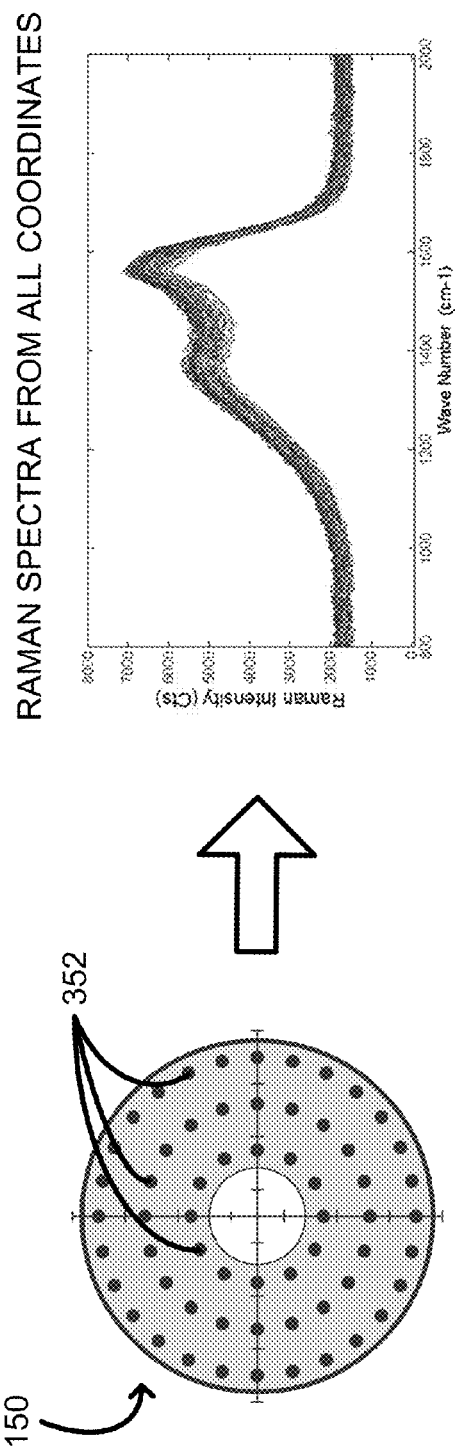

FIG. 3A provides a schematic illustrating automated data collection and analysis according to one or more embodiments.

Figure 3B:
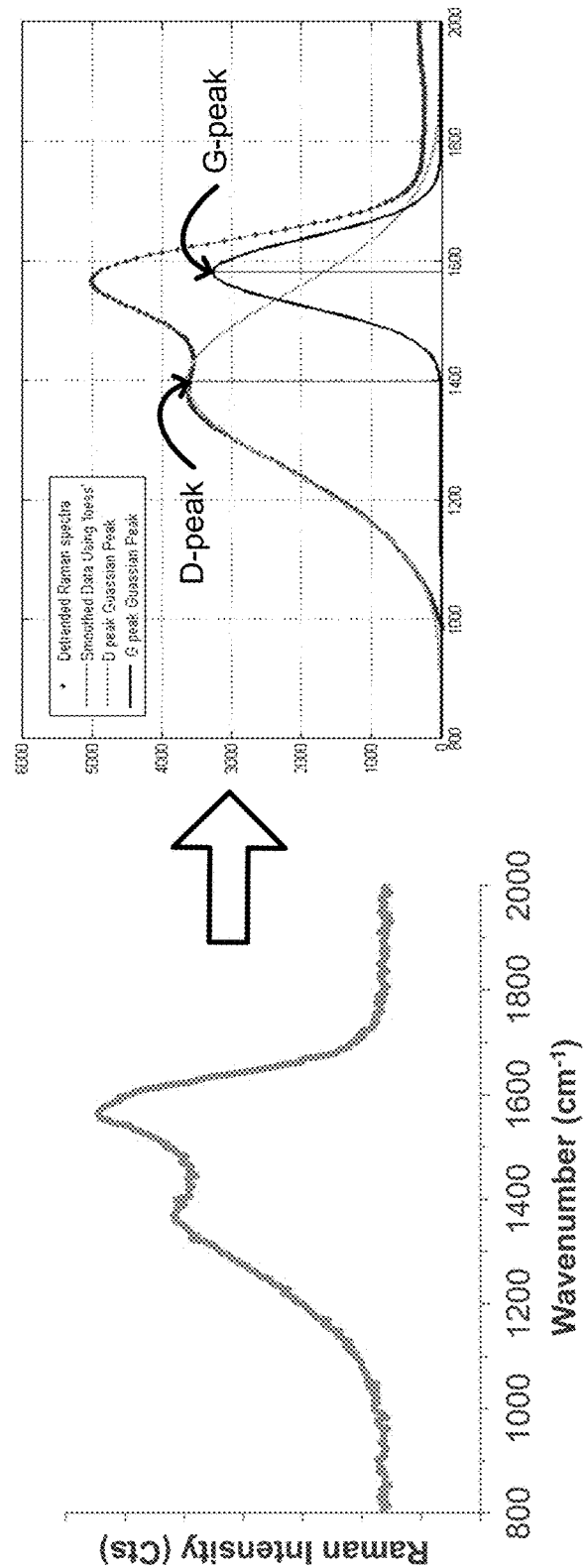

FIG. 3B provides a schematic illustrating automated data collection and analysis according to one or more embodiments.

Figure 4A:
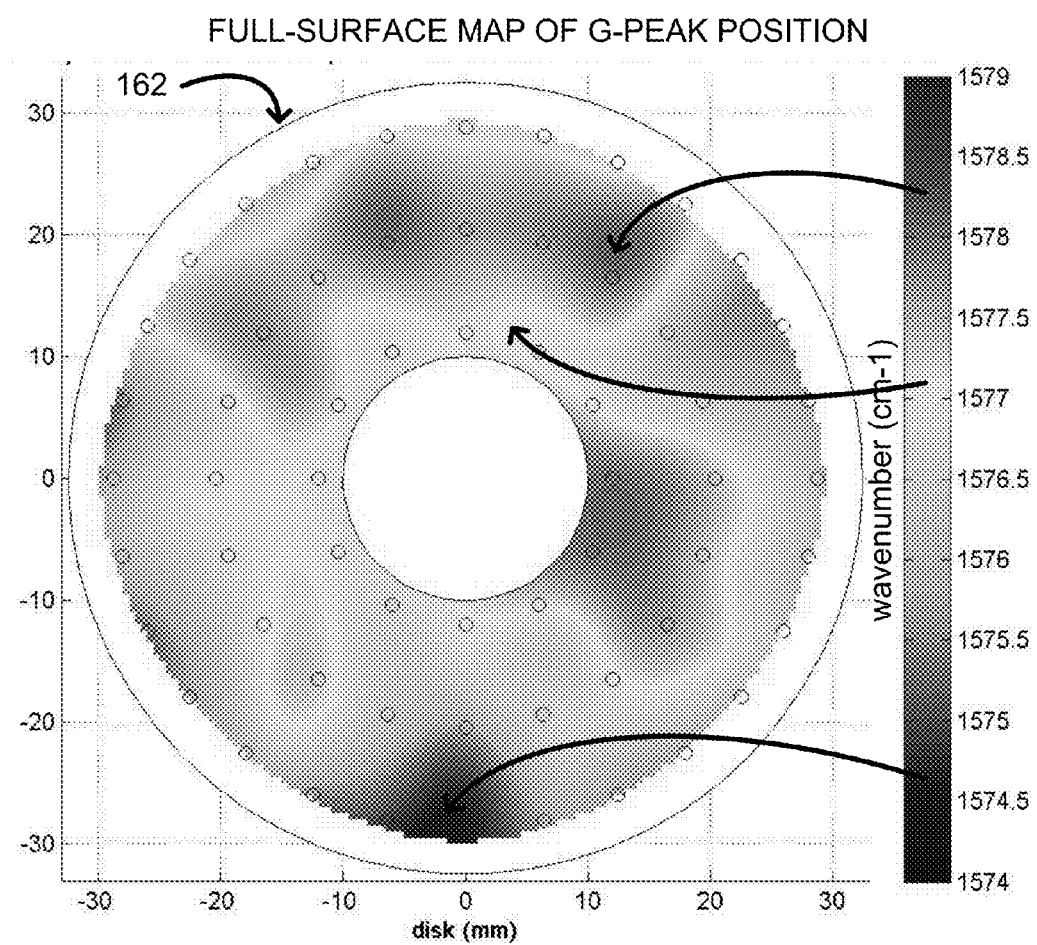

FIG. 4A provides a full-surface Raman map according to one or more embodiments.

Figure 4B:
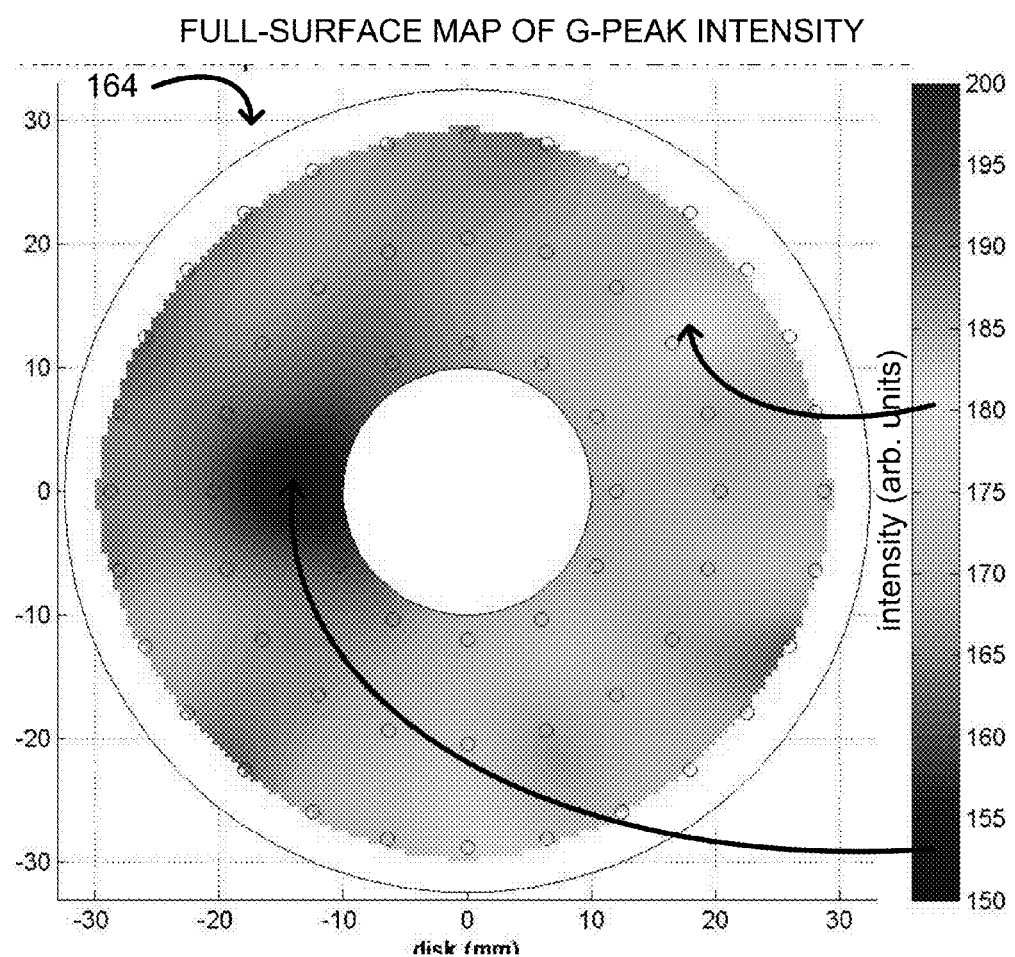

FIG. 4B provides a full-surface Raman map according to one or more embodiments.

Figure 4C:
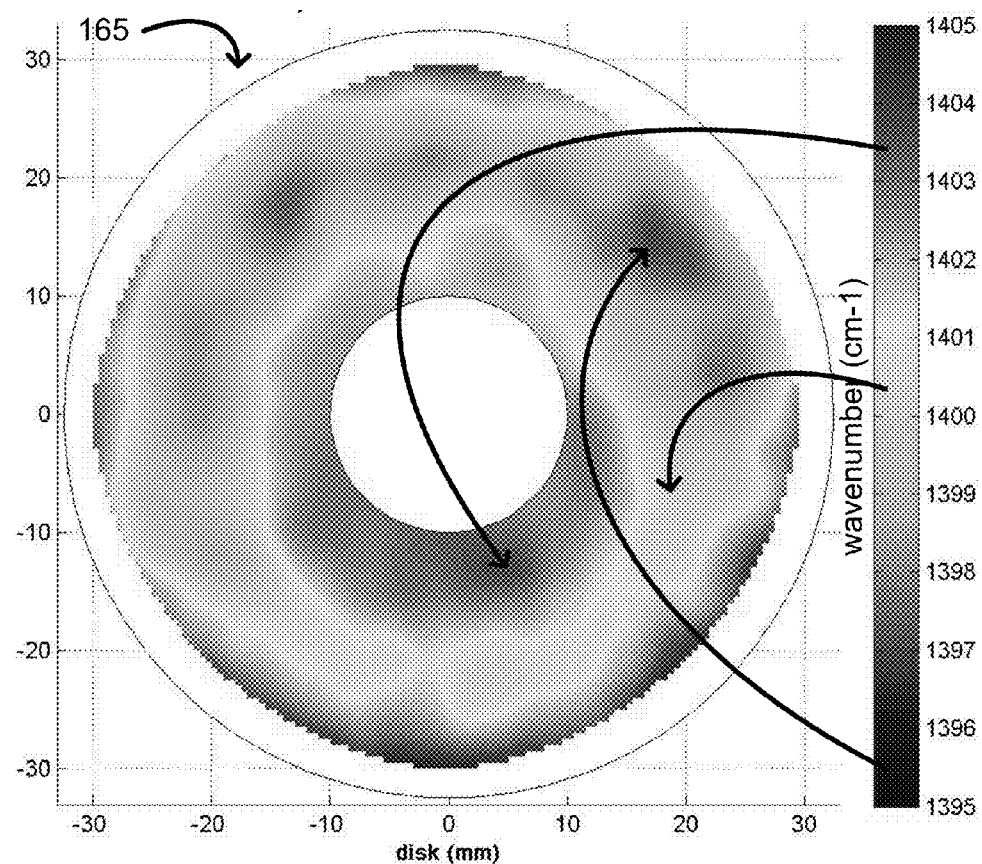

FIG. 4C provides a full-surface Raman map according to one or more embodiments.

Figure 5:
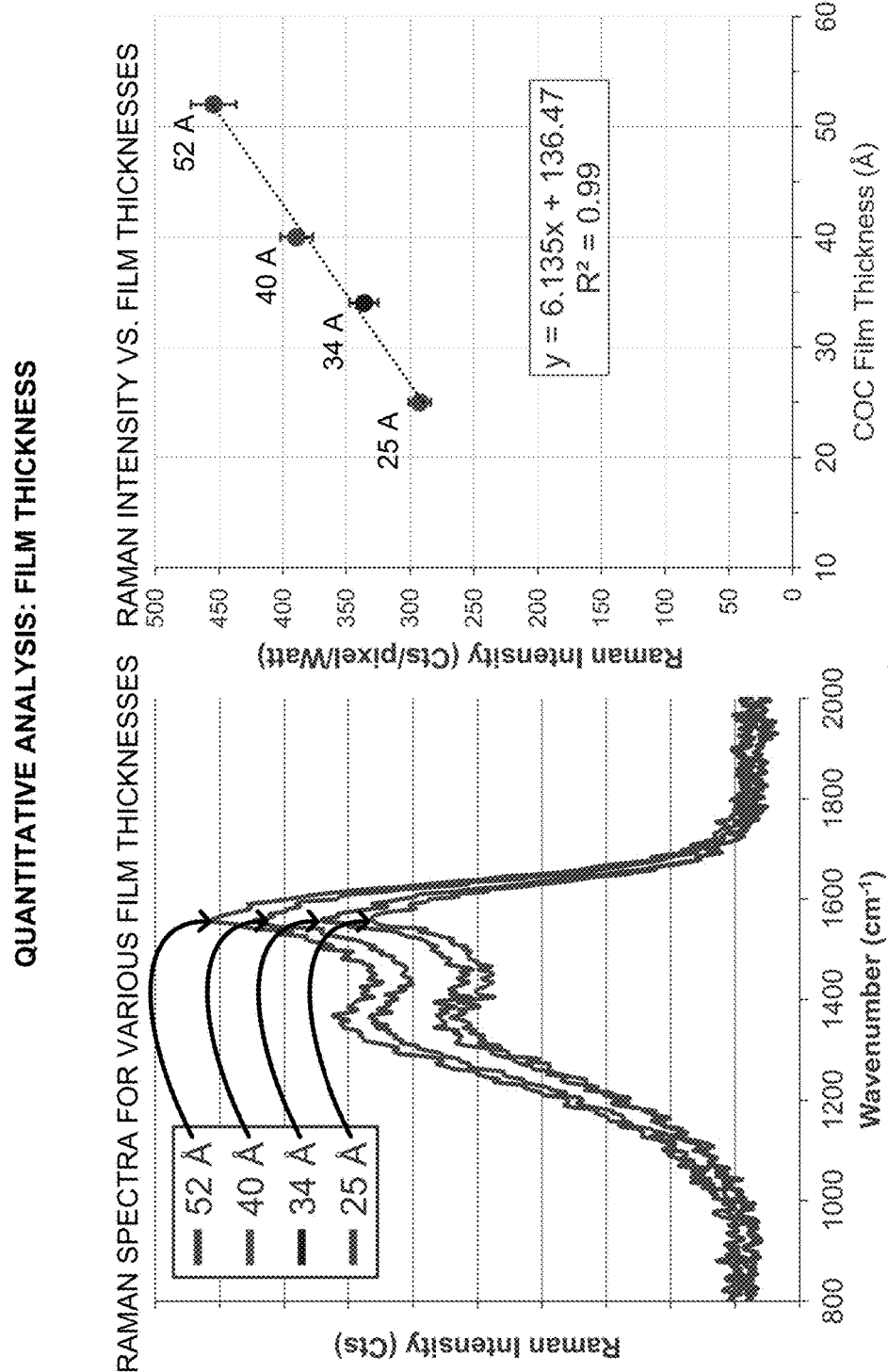

FIG. 5 provides a quantitative analysis of film thickness according to one or more embodiments.

Figure 6:
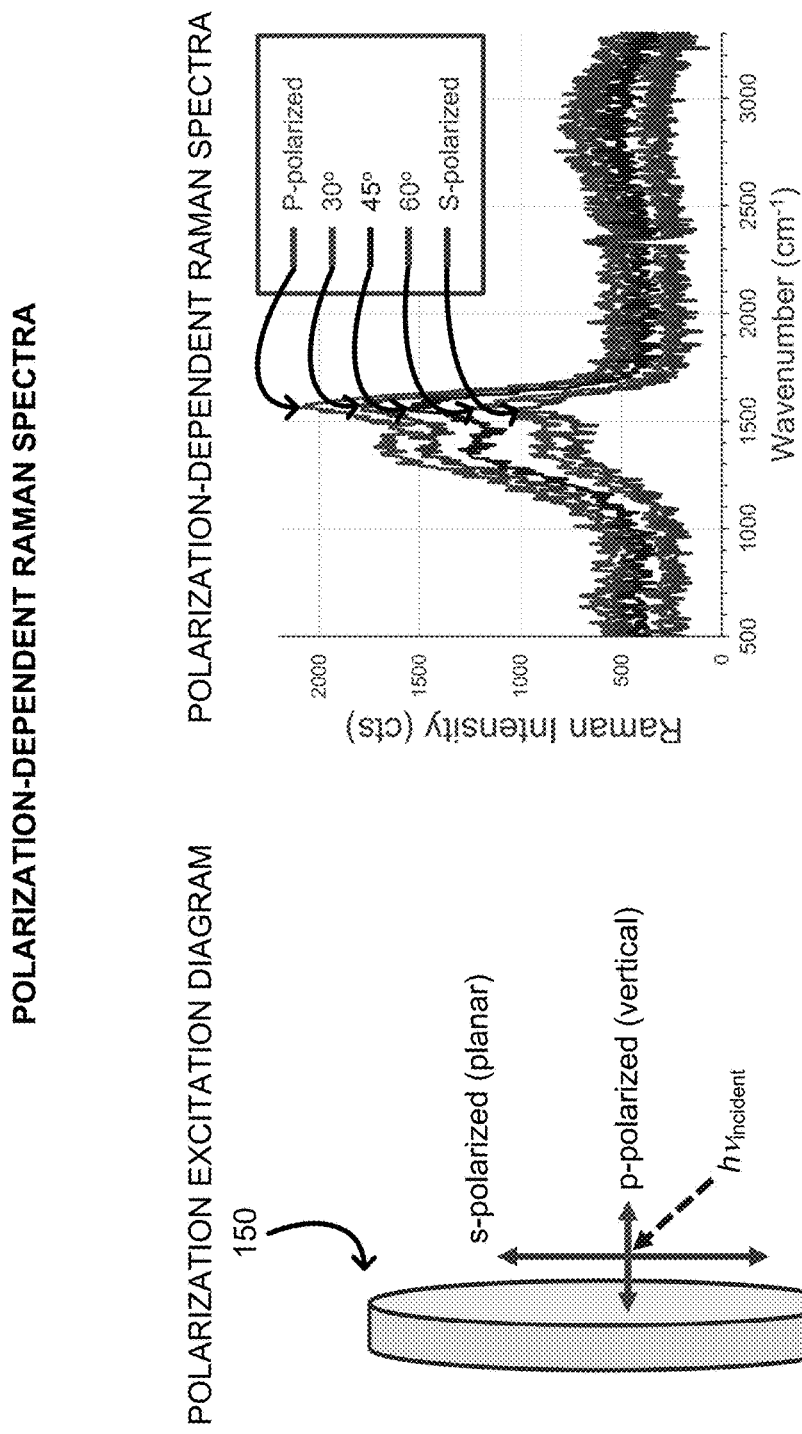

FIG. 6 provides an analysis of polarization-dependent Raman spectra according to one or more embodiments.

DESCRIPTION

Before some particular embodiments are provided in greater detail, it should be understood by those of ordinary skill in the art that the particular embodiments provided herein do not limit the concepts provided herein, as features in such particular embodiments may vary. It should likewise be understood that a particular embodiment provided herein has features that may be readily separated from the particular embodiment and optionally combined with or substituted for features in any of several other embodiments provided herein.

It should also be understood by those of ordinary skill in the art that the terminology used herein is for the purpose of describing some particular embodiments, and the terminology does not limit the concepts provided herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," and "down," or other similar terms such as "upper," "lower," "aft," "fore," "vertical," "horizontal," "proximal," and "distal," or the like, are used for convenience and are not intended to imply, for example, any particular fixed location, orientation, or direction. Instead, such labels are used to reflect, for example, relative location, orientation, or direction. It should also be understood that the singular forms of "a," "an," and "the" include plural references unless the context clearly dictates otherwise.

Unless defined otherwise, all technical and scientific terms used herein have the same meaning as commonly understood by those of ordinary skill in the art.

Conventional Raman apparatuses cannot monitor recording media quality with the throughput (e.g., >~990 pieces per hour) required in recording media production. The conventional apparatuses co-locate excitation optics and collection optics such that incident, excitation light and Raman-scattered light are respectively delivered and collected simultaneously. As a consequence of co-locating the excitation optics and the collection optics, the conventional apparatuses cannot independently control either one of the delivery of the excitation light or the collection of the Raman-scattered light respectively to and from a thin-film surface of a recording medium under inspection. In other words, adjustment of the excitation optics to control the delivery of the excitation light to a thin-film surface of a recording medium also affects the collection optics for the collection of the Raman-scattered light from the surface of the recording medium.

In view of the foregoing, the conventional apparatuses include the following disadvantages: 1) Small excitation light spots (about 1 $\mu m^2$) are produced by focusing light through numerical aperture ("NA") optics, which limits the amount of Raman-scattered light collected from a surface, and which limits the signal throughput of the conventional apparatuses. 2) The small excitation light spots and the limited amount of the Raman-scattered light limits throughput (e.g., 100 seconds for Raman spectroscopy per coordinate). 3) The small excitation light spots have high flux densities, which are known to damage (e.g., burn) thin films of recording media. 4) Reflected excitation light passes directly through the collection optics of the conventional apparatuses, which provides additional sources of unwanted background fluorescence. 5) The incidence or grazing angle of the excitation light cannot be adjusted to specific angles, and the excitation light is fixed to the NA of the collection optics. 6) The polarization of the excitation light cannot be independently controlled between s-polarization and p-polarization.

Provided herein are apparatuses and methods related thereto for analyzing chemical, structural, and/or thickness properties of films such as thin films (e.g., one or more layers of recording media). Apparatuses utilize a configuration including off-axis excitation optics and collection optics for nondestructive Raman spectroscopy methods. Full-surface Raman mapping may be used for analyzing chemical, structural, and/or thickness properties of thin films (e.g., lubricant layers, carbon overcoats, sputtering layers, and defects [e.g., stains] thereof of recording media), including homogeneity of such films. Raman spectra may be collected at a number of coordinates in less than 0.1 seconds per coordinate and subsequently combined for the full-surface Raman mapping.

By decoupling the excitation optics and the collection optics such that the excitation optics and the collection optics are geometrically off-axis from one another, the excitation light (e.g., excitation laser) or the collection of the Raman-scattered light may be independently controlled. For example, the excitation light spot size, spot shape, polarization, etc. may be independently controlled without affecting the collection of the Raman-scattered light. Independent control of the excitation light or the collection of the Raman-scattered light allows for the following: 1) Larger excitation light spots (>>1 $\mu m^2$) at >1000× the excitation light wavelength of the conventional apparatuses, which increases the amount of the Raman-scattered light that may be collected from a surface. 2) In addition to increasing the amount of the Raman-scattered light, the surface area over which Raman scattering occurs may be increased with the larger excitation light spots, which significantly improves throughput (e.g., 0.1 seconds for Raman spectroscopy per coordinate), and which, in turn, allows for full-surface Raman spectroscopy (e.g., <1 minute per entire article) and mapping to be used for analyzing chemical, structural, and/or thickness properties of thin-films (e.g., lubricant layers, carbon overcoats, sputtering layers, and defects [e.g., stains] thereof of recording media), including homogeneity of such films. 3) The larger excitation light spots reduce flux densities (e.g., 1/1000 flux density) below film-damaging levels. 4) The excitation light that is not scattered is reflected off the surface at an angle beyond the NA of the collection optics, which avoids unwanted background fluorescence otherwise produced in the collection optics. 5) The incidence or grazing angle of the excitation light may be adjusted to specific angles that are optimal for particular Raman scattering measurements. 6) The polarization of the excitation light may be independently controlled between 100% s-polarization and 100% p-polarization to allow Raman scattering measurements with greater discrimination of thin-film properties.

FIG. 1 provides a schematic illustrating a Raman apparatus and Raman map according to one or more embodiments.

As shown in FIG. 1, a Raman apparatus 100 may include an off-axis excitation arm 110 including excitation optics and a collection arm 120 including collection optics, the apparatus 100 being configured for analyzing chemical, structural, and/or thickness properties of one or more films such as a thin-film over an article 150. The excitation arm 110 is schematically represented by excitation light $hv_{incident}$ incident upon the article 150, while the collection arm 120 is schematically represented by some collection optics and Raman-scattered light $hv_{scattered}$. Advantageously, due to the off-axis configuration of the excitation arm 110, article-reflected light $hv_{reflected}$ is not collected by the collection arm 120. This reduces or even eliminates unwanted fluorescence otherwise produced in the collection optics, which improves Raman spectra compared to the conventional apparatuses. As further shown in FIG. 1, the apparatus 100 may be configured for producing a Raman map 160 of the thin-film over the article 150.

FIG. 2A provides an annotated image of an excitation arm of a Raman apparatus according to one or more embodiments.

As shown in FIG. 2A, the apparatus 100 may include the off-axis excitation arm 110 including a laser or laser input 212, a laser beam converter 214, an optional laser beam polarizer 216, and one or more laser-focusing elements 218. The laser or laser input 212 may include an optical fiber or free-space laser, and the laser or laser input 212 may include selective polarization in some embodiments. The laser beam converter 214 may include a flat-top laser beam converter for converting a Gaussian excitation light spot to one of uniform intensity (e.g., flat-top excitation light spot shown in FIG. 2A), which may provide non-destructive, uniform laser excitation for Raman scattering. In embodiments comprising the laser beam polarizer 216, the laser beam polarizer 216 may convert between s-polarization (or transverse-electric ["TE"] polarization) and p-polarization (or transverse-magnetic ["TM"] polarization), or otherwise between planar and vertically oriented laser excitation. The laser beam polarizer 216 may also convert between intervening linear polarizations between s-polarization and p-polarization, as well as other polarization forms (e.g., circular, elliptical, etc.). The one or more laser focusing elements 218 may include lenses selected from spherical and cylindrical lenses, which control excitation light spot shape (e.g., circular). In view of the foregoing, a relatively large, uniform, speckle-free excitation light spot may be produced for Raman spectroscopy.

The excitation light spot may be emitted onto a surface of an article at one or more distances and/or angles optimized for Raman spectroscopy of one or more thin films thereof. One angle may be equal to the glancing angle, which is the complement of the angle of incidence, and which angle of incidence is the angle between a ray including the excitation light incident on the surface of the article and the normal (e.g., a line or vector perpendicular to the surface of the article) at the point at which the ray is incident. The glancing angle may also be described as an altitudinal angle or the smallest angle between the ray including the excitation light incident on the surface of the article and the surface of the article at the point at which the ray is incident. In view of the complementary nature of glancing angles and angles of incidence, glancing angles provided herein may instead be expressed as angles of incidence and vice-versa.

The excitation light spot may be emitted onto the surface of the article at a glancing angle ranging from greater than 0° to less than 90°, wherein a glancing angle of 0° represents emitting the excitation light onto the surface of the article from a side of the article, and wherein a glancing angle of 90° represents emitting the excitation light onto the surface of the article from directly above the article. In some non-limiting embodiments, for example, the excitation light may be emitted onto the surface of the article such that the glancing angle is at least 0.01°, 5°, 10°, 15°, 20°, 25°, 30°, 35°, 40°, 45°, 50°, 55°, 60°, 65°, 70°, 75°, 80°, or 85°. In some non-limiting embodiments, for example, the excitation light may be emitted onto the surface of the article such that the glancing angle is no more than 89.99°, 85°, 80°, 75°, 70°, 65°, 60°, 55°, 50°, 45°, 40°, 35°, 30°, 25°, 20°, 15°, 10°, 5°, or 0°. In some non-limiting embodiments, for example, the excitation light may be emitted onto the surface of the article such that the glancing angle is at least 30° or no more than 30°. Combinations of the foregoing may also be used to describe the glancing angle at which the excitation light spot may be emitted onto the surface of the article. In some non-limiting embodiments, for example, the excitation light may be emitted onto the surface of the article such that the glancing angle is at least 0.01° and no more than 89.99° (i.e., between 0.01° and 89.99°), such as at least 0.01° and no more than 45° (i.e., between 0.01° and) 45°, including at least 1° and no more than 35° (i.e., between 1° and 35°). While large glancing angle are possible, large glancing angles (e.g., large glancing angles approaching 90°) may introduce (e.g., by reflection) excitation light to the collection optics, which, in turn, may introduce unwanted fluorescence.

The excitation light spot may include light having a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); polarized light (e.g., linearly polarized light [e.g., s- or p-polarized light], elliptically polarized light, circularly polarized light, etc.), partially polarized light, or nonpolarized light; and/or light with different degrees of temporal and/or spatial coherence ranging from coherent light (e.g., laser) to noncoherent light.

FIG. 2B provides an annotated image of a collection arm of a Raman apparatus according to one or more embodiments.

As shown in FIG. 2B, the apparatus 100 may include the collection arm 120 including a collection lens 222, an optical iris 224, one or more filters 226 including a Raman filter and an optional polarization filter, and a collection fiber 228. The collection lens 222 may include a Raman collection lens including a high NA collection (e.g., 56° half angle). The optical iris 224 may be configured to select a higher-angle portion of the Raman-scattered light from a total of the Raman-scattered light, which facilitates distinguishing between high- and low-angle Raman-scattered light. The Raman filter of the one or more filters 226 may include a long-pass Raman filter for filtering out certain collected laser signals (e.g., Rayleigh scattering), allowing nominal laser transmission for scattered laser analysis. The optional polarization filter may be configured to select between s-polarized and p-polarized Raman-scattered light. The optional polarization filter may also select intervening linear polarizations between s-polarization and p-polarization, as well as other polarization forms (e.g., circular, elliptical, etc.). The collection fiber 228 may include a high NA fiber bundle (e.g., 1.3 mm diameter), which may collect 1000× more in Raman-scattered light than the conventional apparatuses.

As further shown in FIG. 2B, a section A-A of the collection fiber 228 near a Raman-scattering collection end may be round and contain a number of optic fibers. The number of optic fibers, collectively, may collect the Raman-scattered light at each coordinate (see coordinates 352 of the article 150 of FIG. 3A) for a single Raman spectroscopy experiment at each coordinate. Alternatively, for higher resolution, each of the number of optic fibers, individually, may collect the Raman-scattered light at a sub-coordinate at each coordinate for a number of Raman spectroscopy experiments per coordinate. For example, the collection fiber 228 may include 26 optic fibers for 26 Raman spectroscopy experiments at a coordinate. Intermediate resolutions, which may be needed to accommodate a desired throughput, may be effected by groups of adjacent optic fibers, wherein each group of optic fibers (e.g., groups of 2, 3, 4, 5, etc., optic fibers) may collect the Raman-scattered light at a sub-coordinate at each coordinate for a number of Raman spectroscopy experiments per coordinate.

FIG. 2C provides a schematic illustrating a spectrometer for a Raman apparatus according to one or more embodiments.

As shown in FIG. 2C, the apparatus 100 includes a spectrometer (e.g., optical spectrometer) including a spectrograph 230 with imaging optics and a volume phase holographic ("VPH") grating for resolving or diffracting the Raman-scattered light from the collection fiber 228 into different angular output paths for detection by a camera 240 (e.g., charge-coupled device ["CCD"] or complementary metal-oxide semiconductor ["CMOS"] camera).

As further shown in FIG. 2C, a section B-B of the collection fiber 228 near a spectrograph end may be linear and contain the same number of optic fibers discussed in reference to FIG. 2B. For example, the collection fiber 228 may include 26 optic fibers. In view of the foregoing, the collection fiber 228 may include a round-to-linear conversion, wherein the collection fiber 228 is round at the collection arm 120 connection point and linear at the spectrometer connection point. The round-to-linear collection fiber 228 allows the Raman-scattered light to be collected in a circularly shaped area at a coordinate and detected by a linearly oriented array of sensor elements (e.g., a linearly oriented array of CCD sensor elements or CMOS sensor elements).

FIG. 2D provides a schematic illustrating a Raman spectroscopy system for a Raman apparatus according to one or more embodiments.

As shown in FIG. 2D, the apparatus 100 includes a spectroscopy system including the spectrograph 230 and the camera 240 (e.g., CCD or CMOS camera), which includes the linearly oriented array of sensor elements (e.g., the linearly oriented array of CCD or CMOS sensor elements).

The apparatus may further include one or more computers, analyzers, or equivalent devices (e.g., devices that include primary and/or secondary memory and one or more processing elements operable to carry out arithmetic and logical operations), including, but not limited to, servers, workstations, desktop computers, nettops, laptops, netbooks, and mobile devices such as tablets and smartphones, which computers or equivalent devices may contain graphics processing units ("GPU"s), application-specific integrated circuits ("ASIC"s), field-programmable gate arrays ("FPGA"s), etc. The computers or equivalent devices may include a computer-readable storage medium for instructions making the apparatus operable to, but not limited to, perform the methods provided herein.

FIGS. 3A and 3B provide schematics illustrating automated data collection and analysis according to one or more embodiments.

As shown in FIG. 3A, the article 150 may be divided into a number of coordinates 352 for one or more Raman spectroscopy experiments per coordinate, which, in turn, may be used for analyzing chemical, structural, and/or thickness properties of one or more thin films over an entire article 150 (e.g., a carbon overcoat layer of a recording medium). While the coordinates 352 may be in concentric circles as shown, the coordinates 352 may alternatively be arranged in any convenient arrangement for the article 150 and its shape. For example, being that the article 150 is illustrated as annular, another convenient arrangement of the coordinates 352 for the article 150 is a spiral. Whether the coordinates 352 are arranged in concentric circles or a spiral, a spindle motor (not shown) may rotate the article 150 under the collection lens 222, stopping for the collection of the Raman-scattered light at each of the coordinates 352. And while the spindle motor may rotate the article 150 in a start-and-stop or piecewise fashion, it should be understood that continuous rotation (e.g., in a spiral) is also possible.

As further shown in FIG. 3A, the Raman-scattered light from each of the coordinates 352, which may optionally be further divided to include the Raman-scattered light from each optic fiber of the collection fiber 228, may be used to produce Raman spectra for immediate analysis and/or further processing by the one or more computers or equivalent devices.

As shown in FIG. 3B, a Raman spectrum may be further processed to determine, for example, constituent peaks from merged peaks. By means of Gaussian fits, the wavenumbers and intensities for the constituent peaks may be determined and yet further processed (e.g., for full-surface Raman mapping). This is shown in FIG. 3B for a Raman spectrum for a carbon overcoat of a recording medium (e.g., see left-hand Raman spectrum of FIG. 3B), in which the Raman spectrum is processed to provide a constituent G-peak and D-peak (e.g., see right-hand Raman spectrum of FIG. 3B). The G-peak, representing a graphene or graphite film, is shown with a certain wavenumber (e.g., <1600 cm$^{-1}$) and intensity (e.g., >3000 Cts), and the D-peak, representing a disordered graphene or graphite film, is likewise shown with a certain wavenumber (e.g., about 1400 cm$^{-1}$) and intensity (e.g., >3000 Cts). Each Raman spectrum from each optic fiber at each of the coordinates 352 may be processed to extract information such as the foregoing G-peak and D-peak information for full-surface Raman mapping by the one or more computers, analyzers, or equivalent devices.

In various embodiments, computer analyzers, processors, or various other components of apparatus 100 may be used to generate full-surface, vertical anisotropy-resolved map of a thin-film over an article. In some embodiments a spectrograph may be configured to resolve Raman-scattered light collected by collection optics. The spectrograph may be coupled to a processor of apparatus 100 to provide a full-surface spectroscopic analysis of a thin-film over an article. Thus a full-surface spectroscopic analyzer may analyze a thin-film over an article from Raman-scattered light collected by the collection optics.

FIGS. 4A-4C provide full-surface Raman maps according to one or more embodiments.

As shown in FIG. 4A, a full-surface Raman map of G-peak position for a carbon overcoat may be generated from Raman spectra over an entire surface of a recording medium.

As shown in FIG. 4B, a full-surface Raman map of G-peak intensity for a carbon overcoat may be generated from Raman spectra over an entire surface of a recording medium.

As shown in FIG. 4C, a full-surface Raman map of D-peak intensity for a carbon overcoat may be generated from Raman spectra over an entire surface of a recording medium.

The full-surface Raman maps of FIGS. 4A-4C provide examples of at-a-glance analysis of chemical, structural, and/or thickness properties of one or more films over an article.

FIG. 5 provides a quantitative analysis of film thickness according to one or more embodiments.

As shown in FIG. 5, the apparatus 100 is operable to quantitatively analyze film thickness on account of zero-slope baselines in Raman spectra produced by the apparatus 100. The zero-slope baselines result from reduction or elimination of unwanted fluorescence produced in the collection optics.

One or more carbon overcoat layers respectively of one or more recording media, for example, may be quantitatively analyzed with respect to carbon overcoat layer thickness. As shown in FIG. 5, the merged D- and G-peaks characteristic of carbon overcoat layers in recording media may increase in intensity in accordance with carbon overcoat layer thickness. As shown by the Raman spectra in FIG. 5, for example, a 34 Å carbon overcoat layer will have a greater intensity than a 25 Å carbon overcoat layer; a 40 Å carbon overcoat layer will have a greater intensity than a 34 Å carbon overcoat layer; and a 52 Å carbon overcoat layer will have a greater intensity than a 40 Å carbon overcoat layer. Likewise, a 34 Å thick portion of a carbon overcoat layer will have a greater intensity than a 25 Å portion; a 40 Å portion of the carbon overcoat layer will have a greater intensity than a 34 Å portion; and a 52 Å portion of the carbon overcoat layer will have a greater intensity than a 40 Å portion. As further shown in FIG. 5, a plot of Raman intensity (Cts/pixel/Watt) vs. film thickness (Å) indicates a strong linear relationship in at least the range shown. Using such a strong linear relationship, the thickness of the one or more carbon overcoat layers may be determined by the Raman intensity.

Conventional Raman apparatuses cannot detect chemical or physical anisotropy in the planar or vertical dimensions of a thin film such as a thin-film surface of a recording medium. As provided herein, the conventional apparatuses co-locate the excitation optics and the collection optics such that the incident, excitation light and the Raman-scattered light are respectively delivered and collected simultaneously. As a consequence of co-locating the excitation optics and the collection optics, the conventional apparatuses cannot, for example, deliver the excitation light with an electric field component normal to a thin-film surface. Using a carbon overcoat as an example of a thin-film surface of a recording medium, the co-location of the excitation optics and the collection optics prevents selective measurement of chemical anisotropy such as the sp$^2$ bonding that exists in the vertical or planar dimension in the carbon overcoat. In addition, the co-location of the excitation optics and the collection optics prevents selective optical coupling to the underlying substrate morphology of the recording medium, which, in turn, prevents investigation and discrimination of the nanoscale morphology beneath the carbon overcoat.

As provided herein, the apparatus 100 of FIG. 1 may, in some embodiments, include the off-axis excitation arm 110 of FIG. 2A and the collection arm 120 of FIG. 2B, wherein the excitation optics of the excitation arm 110 may include polarization management such as the polarization-selective laser or laser input 212 and the laser beam polarizer 216 (e.g., polarization rotator such as a half-wave plate or a liquid crystal variable retarder), and wherein the collection optics of the collection arm 120 may also include polarization management such as the polarization filter of the one or more filters 226. The polarization management in the off-axis excitation arm 110 may provide the excitation light with s-polarization, p-polarization, or an intervening linear polarization (e.g., 30°-polarization, 45°- or q-polarization, 60°-polarization, etc.), and the polarization management in the collection arm 120 may select from the Raman-scattered light one of the foregoing polarizations. For example, the excitation light may be provided with an electric field component normal to a thin-film surface. Using a carbon overcoat as an example of a thin-film surface of a recording medium, the polarization management in the off-axis excitation arm 110 enables selective measurement of chemical (or physical) anisotropy such as the $sp^2$ bonding that exists in the vertical or planar dimension in the carbon overcoat. In addition, the polarization management in the off-axis excitation arm 110 enables selective optical coupling to the underlying substrate morphology of the recording medium, which, in turn, enables investigation and discrimination of the nanoscale morphology beneath the carbon overcoat.

FIG. 6 provides an analysis of polarization-dependent Raman spectra according to one or more embodiments.

As shown in FIG. 6, the apparatus 100 is operable to analyze (and map) chemical or physical film anisotropy (if not completely isotropic) through two or more of s-polarization, p-polarization, or an intervening linear polarization (e.g., 30°-polarization, 45°- or q-polarization, 60°-polarization, etc.) for the excitation light. S-polarized excitation light is a characteristic of the electric field component of the excitation light being perpendicular to the plane of incidence, and p-polarized is a characteristic of the electric field component of the excitation light being parallel to the plane of incidence. The left-hand side of FIG. 6 shows the s-polarized excitation light to be co-planar with a thin-film surface of the article 150 and the p-polarized excitation light to be perpendicular to the thin-film surface of the article 150, wherein the s-polarized excitation light and the p-polarized excitation light are orthogonal to one another.

A carbon overcoat layer of a recording medium or a portion thereof, for example, may be analyzed with respect to the carbon overcoat layer anisotropy. As shown in FIG. 6, the merged D- and G-peaks characteristic of a carbon overcoat layer in a recording medium may increase in intensity in accordance with excitation light polarization interactions with a particular carbon overcoat layer anisotropy. As shown by the Raman spectra in FIG. 6, for example, the carbon overcoat layer may have a particular anisotropy that does not strongly interact with s-polarized excitation light. However, the carbon overcoat layer may have a particular anisotropy that does interact strongly with p-polarized excitation light. As the electric field component of the excitation light is rotated from that of s-polarization to that of p-polarization (e.g., through 30°-polarization, 45°- or q-polarization, 60°-polarization, etc.), the strong interaction of the carbon overcoat layer and its particular anisotropy with p-polarized excitation light becomes evident.

With respect to articles that may be inspected with apparatuses and methods provided herein, such articles include any article of manufacture or a workpiece thereof in any stage of manufacture having a surface including one or more thin films for which Raman spectroscopic analysis is useful. Thin films may be of any material for which Raman spectroscopic analysis is useful, and the thin films may have a thickness ranging from fractions of a nanometer (e.g., monolayer) to several nanometers (e.g., ≤10 nm), to several ten nanometers (e.g., ≤100 nm), to several hundred nanometers (e.g., ≤1000 nm), to several micrometers. Examples of the articles include, but are not limited to, semiconductor wafers, magnetic recording media (e.g., hard disks for hard disk drives), and workpieces thereof in any stage of manufacture.

TABLE I contrasts the conventional Raman apparatuses with the Raman apparatuses provided herein; however, it should be understood that the contrasts drawn out in Table 1 are examples only.

| | Conventional Raman System | Current Raman System |
|---|---|---|
| Excitation and collection arms: | Co-located | Decoupled/off-axis |
| Vertical and planar excitation using s- or p-polarization: | Only planar | Independently controlled vertical and planar polarization for detecting anisotropy in thin films |
| Laser spot area: | 1 µm² | 10⁶ µm² |
| Laser power: | ~1 mW | 1000 mW |
| Power density: | ~1 mW/µm² | 1 × 10⁻³ mW/µm² for avoiding irreversible damage to film |
| Raman signal throughput: (Laser area × Power Density) | 1x | 1000x for achieving full disk inspection in <1 min |

As such, provided herein is an apparatus comprising an excitation arm comprising excitation optics; a collection arm comprising collection optics, wherein the excitation arm and the collection arm are geometrically off-axis from one another for independent control of the excitation optics or the collection optics; and a processing means for processing Raman-scattered light collected by the collection optics and providing a full-surface spectroscopic analysis of a thin-film over an article. In some embodiments, the excitation optics comprises a laser, a laser beam converter, and a laser focusing element. In some embodiments, the laser beam converter is a flat-top laser beam converter for converting a Gaussian laser beam to a uniformly intense flat-top laser beam. In some embodiments, the apparatus further comprises a polarization-selective laser input and a laser beam polarizer for switching between s-polarized light and p-polarized light. In some embodiments, the excitation optics is configured to provide an excitation laser spot of at least about 1 mm² on a thin-film over an article. In some embodiments, the excitation optics is configured to provide an excitation laser of at least about 1000 mW on a thin-film over an article. In some embodiments, the collection optics comprises an optical iris for selecting a higher-angle portion of the Raman-scattered light from a total of the Raman-scattered light. In some embodiments, the collection optics further comprises a collection fiber, wherein the collection fiber transitions from a round collection fiber at a Raman-scattering collection end and a linear collection fiber at a spectrograph end. In some embodiments, the apparatus further comprises a spectrograph comprising a charge-coupled device camera. In some embodiments, the processing means is further for generating a full-surface, vertical anisotropy-resolved map of a thin-film over an article.

Also provided herein is an apparatus comprising an excitation arm comprising excitation optics; a collection arm comprising collection optics, wherein the excitation arm and the collection arm are geometrically off-axis from one another for independent control of the excitation optics or the collection optics; a spectrograph for resolving Raman-scattered light collected by the collection optics; and a processing means coupled to the spectrograph for providing a full-surface spectroscopic analysis of a thin-film over an article. In some embodiments, the apparatus further comprises a collection fiber, wherein the collection fiber transitions from a round collection fiber at a Raman-scattering collection end and a linear collection fiber at a spectrograph end. In some embodiments, the excitation optics comprises a laser, a flat-top laser beam converter, and a laser focusing element. In some embodiments, the apparatus further comprises a polarization-selective laser input and a laser beam polarizer for switching between s-polarized light and p-polarized light. In some embodiments, the spectrograph further comprises a camera and the processing means is further for generating a full-surface, vertical anisotropy-resolved image map of a thin-film over an article.

Also provided herein is an apparatus comprising an excitation arm comprising excitation optics; a collection arm comprising collection optics, wherein the excitation arm is geometrically off-axis from the collection arm; and a processing means for providing a full-surface spectroscopic analysis of a thin-film over an article from Raman-scattered light collected by the collection optics. In some embodiments, the apparatus further comprises a spectrograph comprising a camera for resolving the Raman-scattered light collected by the collection optics, wherein the processing means is coupled to the spectrograph for providing a full-surface spectroscopic analysis of a thin-film over an article. In some embodiments, the apparatus further comprises a collection fiber, wherein the collection fiber transitions from a round collection fiber at a Raman-scattering collection end and a linear collection fiber at a spectrograph end. In some embodiments, the processing means is further for generating a full-surface, vertical anisotropy-resolved image map of a thin-film over an article. In some embodiments, the excitation optics is configured to provide an excitation laser spot of at least about 1 mm$^2$ on a thin-film over an article. In some embodiments, the excitation optics is configured to provide an excitation laser of at least about 1000 mW on a thin-film over an article.

While some particular embodiments have been provided herein, and while these particular embodiments have been provided in considerable detail, it is not the intention for these particular embodiments to limit the scope of the concepts provided herein. Additional adaptations and/or modifications may readily appear to those of ordinary skill in the art, and, in broader aspects, these adaptations and/or modifications may be encompassed as well. Accordingly, departures may be made from the foregoing embodiments without departing from the scope of the concepts provided herein.

What is claimed is:

1. An apparatus comprising:
   an excitation arm comprising excitation optics, wherein the excitation optics produce light including a range of wavelengths on a thin-film over an article;
   a collection arm comprising collection optics,
      wherein the excitation arm and the collection arm are geometrically off-axis from one another for independent control of the excitation optics or the collection optics; and
   a processor for processing Raman-scattered light collected by the collection optics and providing a full-surface spectroscopic analysis of the thin-film over the article; and
   wherein the collection optics comprises an optical iris for selecting a higher-angle portion of the Raman-scattered light from a total of the Raman-scattered light; and
   wherein the collection optics further comprises a collection fiber, and wherein the collection fiber transitions from a round collection fiber at a Raman-scattering collection end and a linear collection fiber at a spectrograph end; and
   wherein the collection fibers, collectively, collect the Raman-scattered light at coordinates of the article for a single Raman spectroscopy experiment at each coordinate.

2. The apparatus of claim 1,
   wherein the excitation optics comprises a laser, a laser beam converter, and a laser focusing element.

3. The apparatus of claim 2,
   wherein the laser beam converter is a flat-top laser beam converter for converting a Gaussian laser beam to a uniformly intense flat-top laser beam.

4. The apparatus of claim 2, further comprising
   a polarization-selective laser input and a laser beam polarizer for switching between s-polarized light and p-polarized light.

5. The apparatus of claim 1,
   wherein the excitation optics is configured to provide an excitation laser spot of at least about 1 mm$^2$ on the thin-film over the article.

6. The apparatus of claim 1,
   wherein the excitation optics is configured to provide an excitation laser of at least about 1000 mW on the thin-film over the article.

7. The apparatus of claim 1, further comprising
   a spectrograph comprising a charge-coupled device camera.

8. The apparatus of claim 1,
   wherein the processing means is further for generating a full-surface, vertical anisotropy-resolved map of the thin-film over the article.

9. An apparatus comprising:
   an excitation arm comprising excitation optics, wherein the excitation optics produce light including a range of wavelengths on a thin-film over an article;
   a collection arm comprising collection optics,
      wherein the excitation arm and the collection arm are geometrically off-axis from one another for independent control of the excitation optics or the collection optics;
   a spectrograph for resolving Raman-scattered light collected by the collection optics; and
   wherein the collection optics comprises an optical iris for selecting a higher-angle portion of the Raman-scattered light from a total of the Raman-scattered light; and
   wherein the collection optics further comprises a collection fiber, and wherein the collection fiber transitions from a round collection fiber at a Raman-scattering collection end and a linear collection fiber at a spectrograph end; and
   wherein the collection fibers, collectively, collect the Raman-scattered light at coordinates of the article for a single Raman spectroscopy experiment at each coordinate; and
   a processor coupled to the spectrograph for providing a full-surface spectroscopic analysis of the thin-film over the article.

10. The apparatus of claim 9, wherein the excitation optics comprises a laser a flat-top laser beam converter, and a laser focusing element.

11. The apparatus of claim 10, further comprising
a polarization-selective laser input and a laser beam polarizer for switching between s-polarized light and p-polarized light.

12. The apparatus of claim 11,
wherein the spectrograph further comprises a camera, and
wherein the processing means is further for generating a full-surface, vertical anisotropy-resolved image map of the thin-film over the article.

13. An apparatus comprising:
an excitation arm comprising excitation optics configured to provide an excitation laser spot of at least about 1 mm²;
a collection arm comprising collection optics,
   wherein the excitation arm is geometrically off-axis from the collection arm; and
   a processor for providing a full-surface spectroscopic analysis of a thin-film over an article from Raman-scattered light collected by the collection optics; and
wherein the collection optics comprises an optical iris for selecting a higher-angle portion of the Raman-scattered light from a total of the Raman-scattered light; and
wherein the collection optics further comprises a collection fiber, and wherein the collection fiber transitions from a round collection fiber at a Raman-scattering collection end and a linear collection fiber at a spectrograph end; and
wherein the collection fibers, collectively, collect the Raman-scattered light at coordinates of the article for a single Raman spectroscopy experiment at each coordinate.

14. The apparatus of claim 13,
wherein the processing means is further for generating a full-surface, vertical anisotropy-resolved image map of the thin-film over the article.

15. The apparatus of claim 14,
wherein the excitation optics provide the excitation laser spot on the thin-film over the article.

16. The apparatus of claim 13,
wherein the excitation laser spot is at least about 1000 mW on the thin-film over the article.

* * * * *